United States Patent [19]

Lares et al.

[11] Patent Number: 4,521,189
[45] Date of Patent: Jun. 4, 1985

[54] DENTAL HANDPIECE

[75] Inventors: Joseph P. Lares, Redwood City; Mark Cowell, San Carlos, both of Calif.

[73] Assignee: Lares Research, San Carlos, Calif.

[21] Appl. No.: 548,431

[22] Filed: Nov. 3, 1983

[51] Int. Cl.³ ............................................... A61C 1/10
[52] U.S. Cl. ...................................... 433/84; 433/126
[58] Field of Search ....................... 433/126, 82, 84, 98

[56] References Cited

U.S. PATENT DOCUMENTS 4,173,827 11/1979 Austin, Jr. .............................. 433/98
4,353,697 10/1982 Nakanishi ............................. 433/126
4,403,959 9/1983 Hatakeyama ....................... 433/126

Primary Examiner—John J. Wilson
Attorney, Agent, or Firm—Lothrop & West

[57] ABSTRACT

A dental handpiece includes two hollow casings arranged to swivel with respect to each other about an axis. A hub connected to one casing has a carefully finished exterior surface that has a close fit with a surrounding interior surface on the other casing. Various grooves around the hub are supplied with turbine drive air, with water and with auxiliary air. Registering ports in the other casing conduct these fluids to the vicinity of an air turbine at the end of the other casing. No O-rings or comparable seals are used between the fluid connections at the hub, but the positioning of the several grooves and ports and the relative pressures of the fluids are arranged so that any minor leakage is not harmful.

8 Claims, 9 Drawing Figures

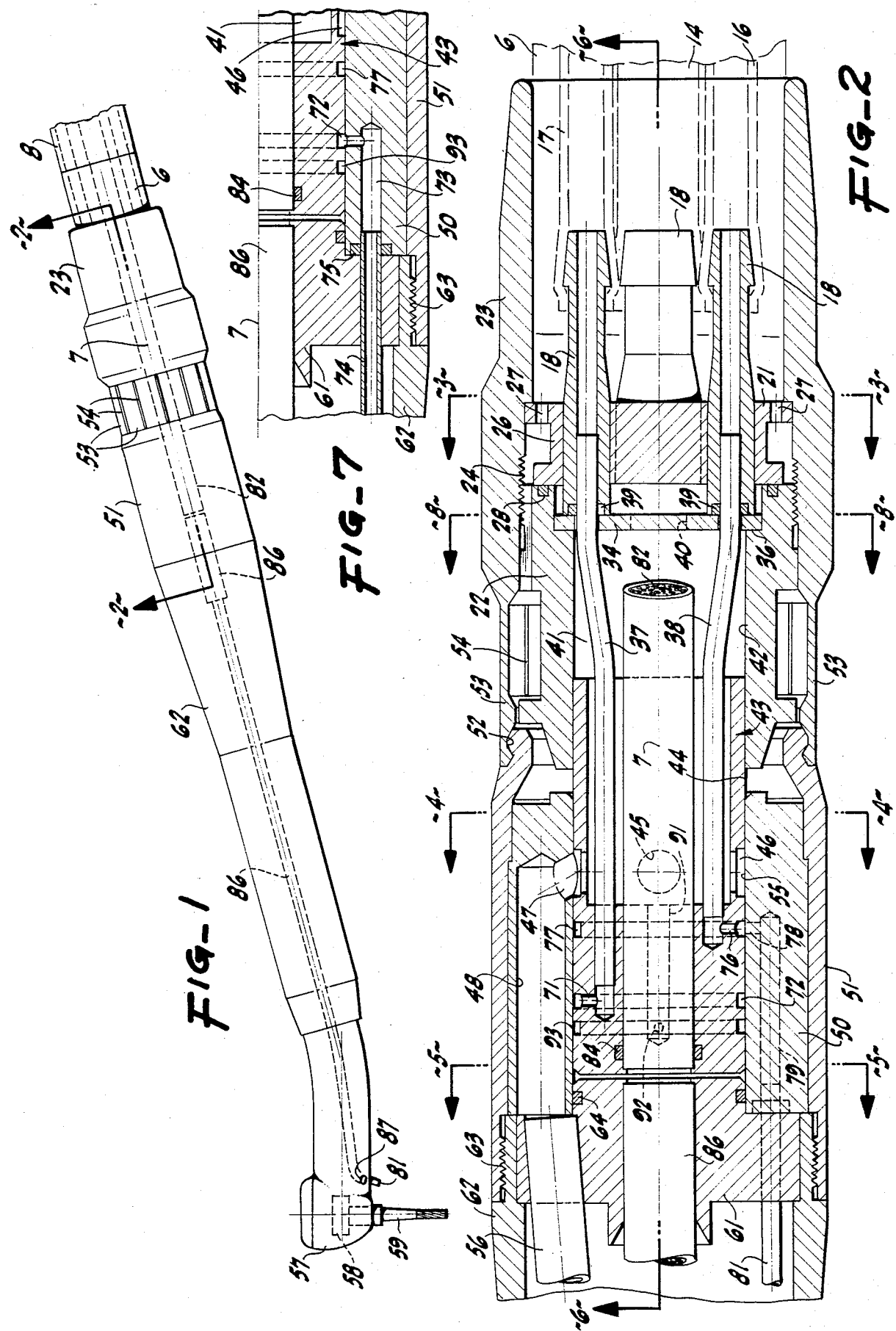

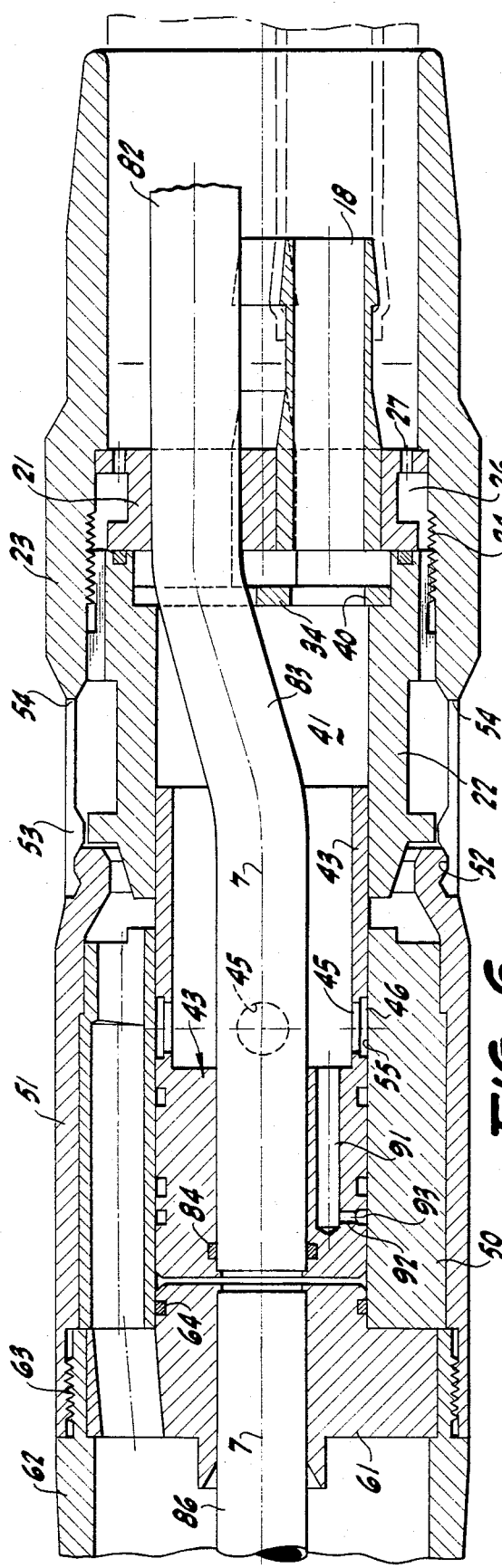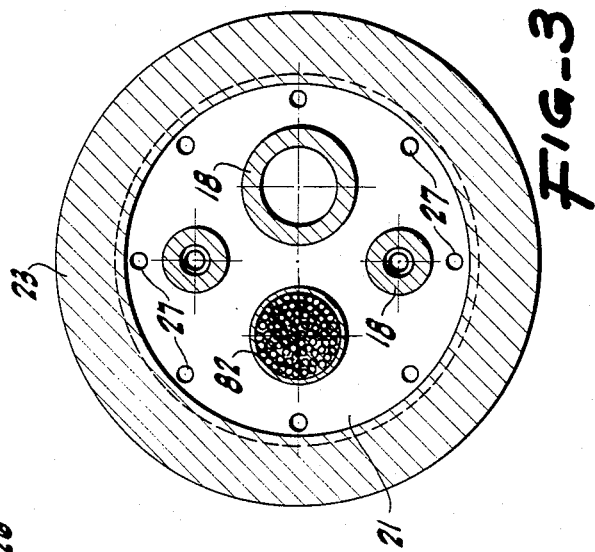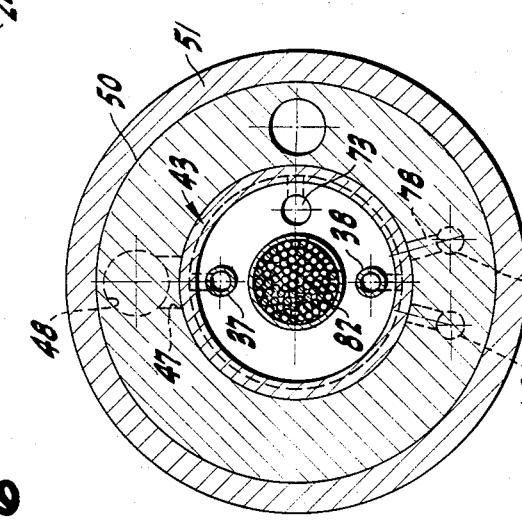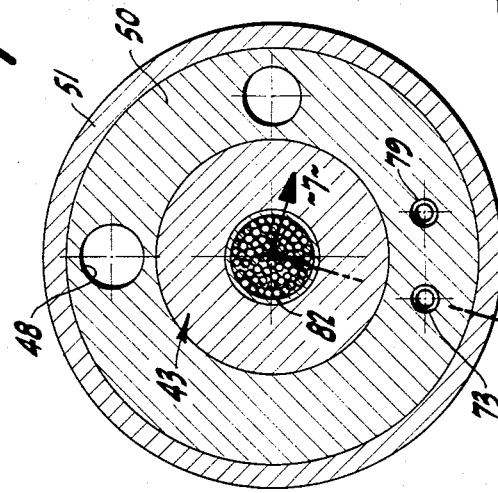

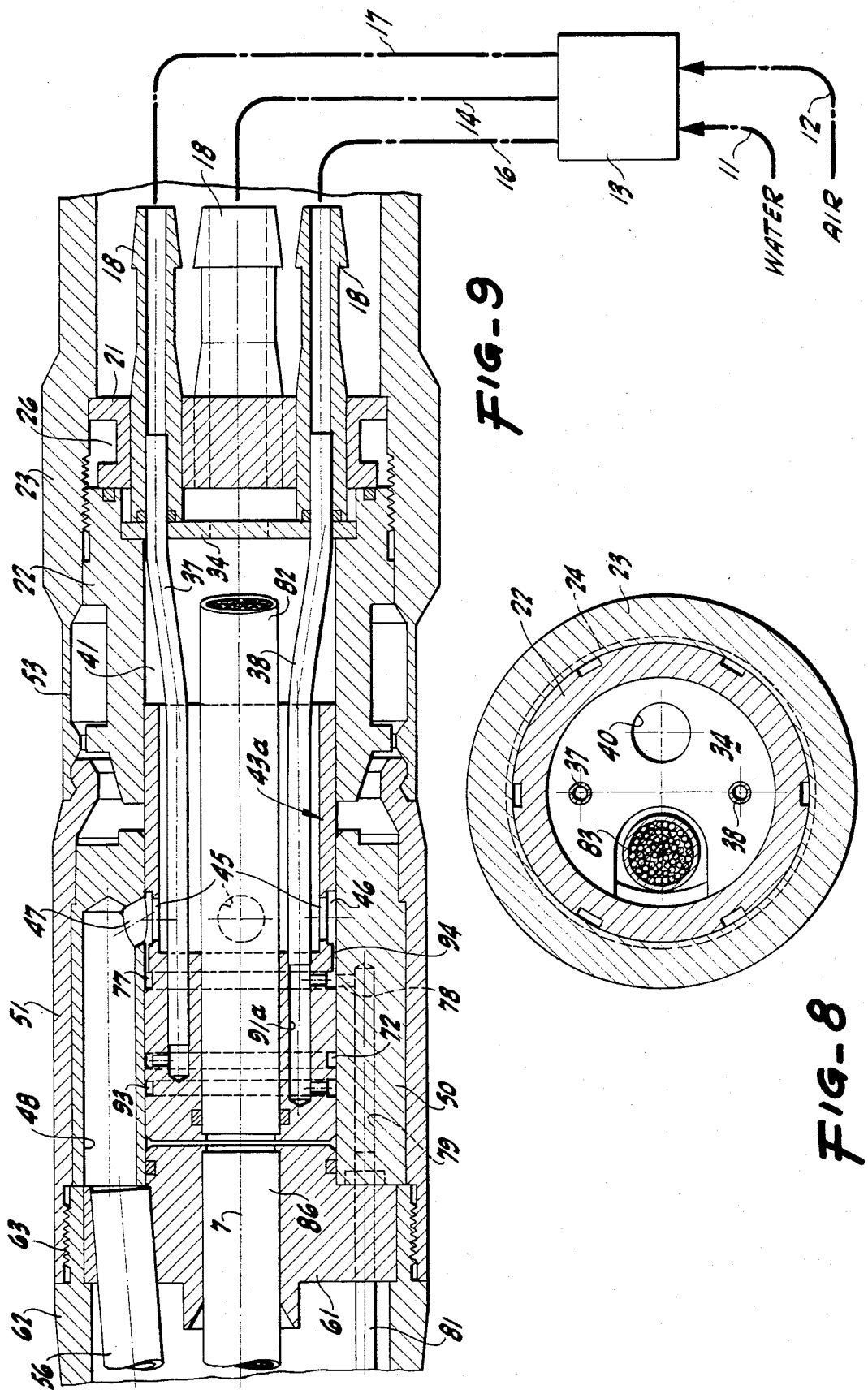

4,521,189

DENTAL HANDPIECE

CROSS-REFERENCE TO RELATED APPLICATIONS

Reference is particularly made to the application of Joseph P. Lares, Ser. No. 502,492, filed June 9, 1983 and entitled "Swivel Dental Handpiece".

BRIEF SUMMARY OF THE INVENTION

A dental handpiece includes a pair of coaxial, swivelling hollow casings connected at one end to a supply hose and at the other end to an air turbine driving a dental bur. A supply of turbine driving air, a supply of auxiliary air, and a supply of water are all conducted through the swivel portion of the handpiece. The two portions of the handpiece turn about a longitudinal axis with the two portions of the casings meeting each other in a relatively close, virtually metal-to-metal contact. More particularly, the water connection between the two swivelling parts of the handpiece is disposed axially between two end connections for the main driving air. The auxiliary air connection between the two swivelling portions of the handpiece is also interposed between the endmost connections for driving air. The driving air at the air interconnections is maintained at a higher pressure at the water interconnection than the water. In this way it is possible to omit any frictional sealing members such as packings or O-rings between the various fluid conducting portions. There is no deleterious leakage, and the dental handpiece is simplified and swivels easily.

PRIOR ART

In the above-identified application there is an extensive listing of prior art, which is incorporated herein by reference. This is the closest prior art known to the applicants.

BRIEF DESCRIPTION OF THE SEVERAL VIEWS OF THE DRAWINGS

FIG. 1 is a side elevation of a dental handpiece constructed in accordance with the invention and indicating the exterior appearance thereof.

FIG. 2 is a cross-section to a greatly enlarged scale along the axis of a portion of the handpiece structure, the plane of section being indicated by the line 2—2 of FIG. 1.

FIG. 3 is a cross-section, the plane of which is indicated by the line 3—3 of FIG. 2.

FIG. 4 is a cross-section, the plane of which is indicated by the line 4—4 of FIG. 2.

FIG. 5 is a cross-section, the plane of which is indicated by the line 5—5 of FIG. 2.

FIG. 6 is an axial cross-section, the plane of which is indicated by the line 6—6 of FIG. 2.

FIG. 7 is a cross-section, the plane of which is indicated by the line 7—7 of FIG. 5.

FIG. 8 is a cross-section, the plane of which is indicated by the line 8—8 of FIG. 2.

FIG. 9 is a cross-section, comparable to FIG. 2, but showing a modified form of device.

DETAILED DESCRIPTION

In one form of a dental handpiece pursuant to the invention there is afforded a boss 6 of symmetrical about a longitudinal axis 7 and connected in the customary way to a multipart hose 8 leading to remotely controlled supplies of water, of drive air and of auxiliary air. These are respectively derived in a standard fashion, as shown in FIG. 9, from a suitable water supply 11 and an air supply 12 extending through a pressure regulating and operator controlled element 13. Drive air is furnished through a conduit 14, and auxiliary air is furnished through a conduit 16 to supply at will a flow of spray assist or chip air. Water is supplied through a conduit 17.

From the hose 8 the various conduits 14, 16 and 17 are appropriately connected to barbed fittings 18 all supported in a disc 21 clamped between one end of a first hollow casing 22 and a securing sleeve 23 detachably engaging the casing 22 by a threaded connection 24. The disc 21 has a peripheral groove 26 in communication with the interior volume of the sleeve 23 through a number of apertures 27 and is sealed against the casing 22 by an O-ring 28. The ends of the various fittings 18 for the respective conduits 16 and 17 are well seated in the disc 21 and the fittings 16 and 17 butt against an end plate 34 abutting a shoulder 36 in the casing 22. Two of the fittings 18 receive individual conduits 37 and 38 sealed by O-rings 39 interposed between the end plate 34 and the ends of the respective fittings 18. The drive air fitting 18 is similarly seated in the disc 21 and simply opens through an aperture 40 (FIG. 8) in the end plate 34 to an interior volume 41 within the casing 22.

Seated with a press fit in an interior bore 42 in the casing 22 is a hub 43 extending along the axis 7 and having a very carefully finished exterior, circular-cylindrical surface 44. The chamber 41 extends well into the interior of the hub 43. Drive air under pressure from the chamber 41 within the interior of the hub 43 can flow outwardly through ports 45 into a groove 46 around the hub. From the groove 46 drive air flow is through a drilled passage 47 into a drive air passage 48 disposed eccentrically of and parallel to the axis 7 in a sleeve 50 within a second hollow casing 51 concentric with the axis.

The second casing 51 has a peripheral groove 52 with which engage a number of spring fingers 53 separated by a number of slits 54 and projecting from the sleeve 23. With this arrangement the second casing 51 with its sleeve 50 and the first casing 22 with its sleeve 23 can be brought into alignment and interconnection with the springiness of the fingers 53 holding the parts in assembled position. Relative rotation or swivelling of the sections is free. Yet, a strong enough separating pull on the individual pieces causes the spring fingers 53 to yield and permits the parts to separate with the sleeve 50 pulling axially off of the hub 43. Reverse thrust accomplishes assembly.

The interior of the second sleeve 50 tightly encloses the hub 43 and has an internal surface 55 well finished to fit with only slight clearance or tolerance against one surface 44 on the hub 43. There is free relative rotation of the parts about the axis 7 and there is easy, axial connecting and disconnecting relative motion therebetween. The small clearance space (viz. 0.0001 inch) is preferably such as that produced by lapping of the parts during manufacture.

The air passage 48 in the sleeve 50 in all rotated positions of the parts is open to the chamber 41 and leads into and communicates with a conduit 56 extending along the interior of the second casing and to the interior of a turbine housing 57. This is at the end of the secondary casing 51. The conduit at its end serves as an air nozzle for the rotor 58 of an air turbine for driving a dental bur 59.

The conduit 56 is partially supported in an end plate 61 clamped between one portion of the second casing 51 and an extension 62 thereof by a threaded interconnection 63. An O-ring 64 precludes leakage between the sleeve 50 and the end plate 61.

To afford an appropriate internal water connection, the conduit 37 extends through the chamber 41 (shown in the upper part in FIG. 2) and into the closed end of the hub 43 wherein it terminates. A cross bore 71 opens into a peripheral groove 72 (see also FIG. 7) on the hub 43. The cross bore 71 is carefully chosen as a restrictor to help control the pressure of water in the groove 72. While the pressure regulating element 13 affords a control of the water pressure in the conduit 17 and the conduit 37, the important factor is to provide the cross bore 71 to furnish a resistance so that the pressure of the water in the groove 72 itself is at a selected or chosen value. The groove 72 opens to a radial and axial water duct 73 (FIG. 7) from which a conduit 74, sealed by an O-ring 75, extends to and discharges from the handpiece near the bur 59.

In a somewhat similar fashion, the auxiliary air conduit 38 extends through the chamber 41 (see the lower part of FIG. 2) and terminates with a closed end in the hub 43. A radial opening 76 leads into a groove 77 encompassing the hub 43. The opening 76 is carefully chosen as a restrictor to assist in controlling the pressure of the air derived from the regulating element 13 and received in the groove 77. That is, the opening 76 is selected so as to ensure that the air pressure in the groove 77 is of a known or selected value greater than the selected water pressure as measured in the groove 72. The groove 77 communicates in all rotated positions of the parts across the clearance space with a bore 78 leading to a longitudinal auxiliary air passage 79 opening into a duct 81 extended to discharge from the handpiece adjacent the dental burr 59.

In addition, there is carried through the swivelling handpiece an optical conductor having an inlet lead 82 (FIG. 6) extended from a remote and appropriate source. The lead travels with an offset 83 to lie along the axis 7 and to extend through the chamber 41 and through the hub 43. The optical conductor is sealed by means of an O-ring 84. The end of the inlet lead 82 is squared and, over a minute gap, faces the similar end of a comparable fiber optic lead 86 extending along the axis. The lead 86 usually is divided and exits in optical terminals 87 near the bur 59.

The fiber optic lead 86 where it goes through the end plate 61 may be a tight, non-leaking fit so that with the O-ring 64 the end plate acts as a complete barrier to downstream flow of any leakage from the grooves in the hub 43. But if it is desired to keep the pressure between the facing ends of the hub 43 and the end plate 61 at a low value, then the fiber optic lead 86 can be only loosely fitted into the end plate 61 to allow substantial clearance or flow space therebetween. In this case, the O-ring 64 and its groove can be omitted. Any flow between the fiber optic lead 86 and the end plate 61 can continue into the interior of the extension 62 and from there a connecting passage (FIG. 6) to the atmosphere at the slits 54.

Particularly pursuant to the invention, some of the drive air from the chamber 41 is led through an axial duct 91 (FIG. 2) into a cross duct 92 and to a peripheral groove 93 surrounding the hub 43 on the axially opposite side of the water groove 72 from the drive air groove 46. Again, the cross duct 92 is carefully chosen so that its effect on the air flowing into the groove 93 is to assure that the air pressure in the groove 93 is at a value higher than the pressure of the water in the groove 72. Thus, drive air at a pressure or pressures higher than the pressure of the water in the groove 72 is available in the grooves 77 and 93 near both ends of the hub 43 and opposite sides of the water groove 72. Some leakage may occur in the absence of O-rings or other seals. But there is no leakage of relatively low pressure auxiliary air or water toward the relatively high pressure end, drive air grooves. If there is some leakage in the opposite direction from the drive air grooves toward and into the auxiliary air groove, that leakage air simply mixes with the auxiliary air and is of no consequence. Also, if there is some leakage of air from the drive air grooves into the water groove, again there is only a harmless admixture. Thus, with this arrangement leakage is inconsequential, and seals such as O-rings can be omitted from the swivelling interconnections.

With this same general arrangement, it is sometimes helpful to make some alterations in the air flow paths. As shown especially in FIG. 9, most of the structure is as previously described, but the hub 43a is varied by affording communication between the main drive air groove 46 and the adjacent auxiliary air groove 77. This is done by leaving a substantial annular clearance 94 between them. This construction allows some interchange of the main drive air and the auxiliary air. Also, the axial duct 91 is replaced by an axial duct 91a, opening into the groove 93, as before, and communicating with the auxiliary air conduit 38 instead of the chamber 41.

With the FIG. 9 arrangement, when main drive air is supplied to the turbine, some leaks through the clearance 94 into the groove 77 to discharge as auxiliary air. Any air leaking from the end groove 93 and between a loose lead 86 and the end plate 61 serves as an air lubricant for the swivelling surfaces. If main air is not being supplied but auxiliary air is being supplied, then there may be some auxiliary air leakage from the groove 77 to the groove 46 through the annulus or clearance 94. This auxiliary air leakge into the drive air groove 46 is normally insufficient to operate the turbine.

I claim:

1. A dental handpiece comprising a metal hub symmetrical about an axis and having a circular-cylindrical homogeneous exterior surface, a first hollow casing symmetrical about said axis and secured to said hub, a metal second hollow casing having a circular-cylindrical homogeneous interior surface, means mounting said second hollow casing with said interior surface on said second casing adjacent said exterior surface on said hub with only sufficient clearance space therebetween to rotate relative thereto about said axis, means on said hub defining a plurality of axially spaced grooves open to said exterior surface and open to said interior surface on said second hollow casing, means in said first hollow casing and extending within said hub to the endmost ones of said axially spaced grooves for conducting air to said endmost grooves at a relatively high pressure in said endmost grooves, means in said second hollow casing for conducting said air away from at least one of said endmost grooves, means in said first hollow casing and extending within said hub to one of said grooves intermediate said endmost grooves for conducting water to said intermediate groove at a relatively low pressure in said intermediate groove, and means in said second hollow casing for conducting said water away from said intermediate groove, whereby the clearance space between the casings and the difference in pressure between the air in said endmost grooves and the water in said intermediate groove serve to substantially confine the water to said intermediate groove.

2. A device as in claim 1 including a fluid pressure controller for supplying fluids to said grooves with the pressures of said fluids in said grooves at selected pressures.

3. A device as in claim 1 including a fluid pressure controller for supplying air to said endmost grooves at a relatively high pressure therein and for supplying water to an intermediate one of said grooves at a relatively low pressure therein.

4. A device as in claim 1 in which said interior surface on said second hollow casing is journalled to turn on said exterior surface on said hub solely with metal-to-metal contact.

5. In a device as in claim 1, means for supplying water at a predetermined pressure to a water passage in said hub connected to a receiving water passage in said second hollow casing across the clearance space therebetween in all relative rotated positions of said hub and said second hollow casing about said axis, and means in said hub on both sides axially of said water passages for subjecting said clearance space to air at a pressure higher than said predetermined pressure.

6. A dental handpiece comprising a first casing symmetrical about an axis, a hub extending coaxially from said first casing and having an exterior circular-cylindrical surface concentric with said axis, means forming a plurality of axially spaced fluid outlets in said exterior surface, a second casing symmetrical about said axis, a sleeve extending coaxially within said second casing and having an interior circular-cylindrical surface journalled with uniform rubbing clearance in said exterior circular-cylindrical surface, means in said sleeve forming a plurality of axially spaced fluid inlets in said interior surface and respectively adapted to communicate with said outlets, means for supplying fluid at a relatively high pressure to the endmost ones of said outlets, and means for supplying fluid at a relatively low pressure to intermediate ones of said outlets, whereby the clearance space between the casings and the difference in pressure between the fluid in said endmost outlets and the fluid in said intermediate outlets serve to substantially confine the fluid in said intermediate outlets.

7. A device as in claim 6 in which said clearance space between said interior circular-cylindrical surface and said exterior circular-cylindrical surface is substantially uniform and unobstructed for the entire axial dimension of said surface.

8. A device as in claim 6 in which said uniform rubbing clearance is substantially 0.0001 inch.

* * * * *